(12) United States Patent
Seul et al.

(10) Patent No.: US 7,363,170 B2
(45) Date of Patent: Apr. 22, 2008

(54) TRANSFUSION REGISTRY NETWORK PROVIDING REAL-TIME INTERACTION BETWEEN USERS AND PROVIDERS OF GENETICALLY CHARACTERIZED BLOOD PRODUCTS

(75) Inventors: Michael Seul, Fanwood, NJ (US); Robert James Danegy, Libertyville, IL (US)

(73) Assignee: Bio Array Solutions Ltd., Warren, NJ (US)

( * ) Notice: Subject to any disclaimer, the term of this patent is extended or adjusted under 35 U.S.C. 154(b) by 420 days.

(21) Appl. No.: 11/092,420

(22) Filed: Mar. 29, 2005

(65) Prior Publication Data

US 2006/0008859 A1    Jan. 12, 2006

Related U.S. Application Data (60) Provisional application No. 60/586,931, filed on Jul. 9, 2004, provisional application No. 60/621,196, filed on Oct. 22, 2004.

(51) Int. Cl.
*G06F 17/00* (2006.01)
*C12Q 1/68* (2006.01)

(52) U.S. Cl. ............................... 702/19; 702/20; 435/6

(58) Field of Classification Search ...................... None
See application file for complete search history.

(56) References Cited

U.S. PATENT DOCUMENTS 6,014,451 A    1/2000    Berry et al.

6,650,703 B1    11/2003    Schwarzmann et al.

OTHER PUBLICATIONS

Filipovich et al, Blood 97 (6), 1598-1603 (2001).*
Storry et al, British Journal of Haematology 126: 759-770 (2004).*
Schreiber GB et al. "Increasing Blood Availability by Changing Donation Patterns" Transfusion 43:591-7 (2003).

* cited by examiner

*Primary Examiner*—James Martinell
(74) *Attorney, Agent, or Firm*—Eric P. Mirabel (57) ABSTRACT

Disclosed is a registry system, including member institutions, in which transfusion donors and recipients are registered following genotyping, which would typically take place in a member institution, or a member institution would have access to the genotyping information, if performed outside. The registry database can be accessed and searched by members seeking samples of particular type(s). Systems are disclosed for maintaining economic viability of genotyping in connection with transfusions, by maximizing the number of units placed with the minimal number of candidate donors typed. Genotyping of potential donors, and product supply, is matched to forecasted demand. Genotyping can also be limited to the more clinically relevant markers. The registry system can also be integrated with one format of assay which generates an image for analysis, whereby the imaged results can be analyzed and redacted by experts in a central location, and then transmitted back to the patient or their representative.

2 Claims, 8 Drawing Sheets

TRANSFUSION REGISTRY NETWORK PROVIDING REAL-TIME INTERACTION BETWEEN USERS AND PROVIDERS OF GENETICALLY CHARACTERIZED BLOOD PRODUCTS

RELATED APPLICATIONS

This application claims priority to U.S. Provisional Application Ser. Nos. 60/586,931 filed Jul. 9, 2004 and 60/621,196 filed Oct. 22, 2004.

BACKGROUND

The prevailing paradigm of organizing the supply of blood units available for transfusion relies on routine typing of transfusion antigens by hemagglutination. Typically, the major transfusion antigen groups, namely A, B, O and D, are typed at collection while a select set of minor group antigens such as RhCE, Kell and Kidd are typed only as needed For blood group antigens other than ABO and D, source material is diminishing, and the cost of FDA-approved commercial reagents is escalating. Many antibodies used for testing for minor blood group antigens (especially when searching for an absence of a high prevalence antigen) are not FDA-approved and are characterized to varying degrees by those who use them. In addition, some antibodies are limited in volume, weakly reactive, or not available. Collectively, the labor-intensive approach limits the number of donors one can test; thereby restricting the supply of antigen-negative RBC products for patients who have produced the corresponding alloantibody, and, more recently, restricting the supply of Rh and K matched RBCs for patients in the Stroke Prevention Trial (STOP) program, which was designed to prevent immunization of such patients.

Recipients exposed to foreign transfusion antigens generally will form antibodies directed against those antigens. Allo-immunized patients, a subpopulation comprising approximately 2% of transfused patients, and up to 38% of multiply transfused patients, require red blood cell products which do not contain the offending antigen. Such units typically must be found either in the limited available supply or must be found, in real time, by serological typing of such likely candidate units as may be available in inventory. The selection of candidate units for "stat" typing, performed in immunohematology laboratories, is guided largely by empirical factors. The delay introduced by the search for matching units can exacerbate emergency situations and generally will incur substantial cost to hospitals and/or insurance carriers by delaying in-hospital stay. More generally, allo-immunization to red blood cell antigens which are also displayed on other cells (see Table I) and recognized by certain pathogens such as malaria, can introduce unnecessary health risks whose elimination would improve the general health.

The procurement of matched blood to recipients who either display an uncommon antigen or lack a common antigen, is particularly problematic. While such incidences are considered "rare," occurring at a rate of one in 1,000 recipients, the supply of matched units is very limited. Thus, existing national collections of special units, including the American Rare Donor Program (ARDP), register donors encountered in the immunohematology laboratories of its members: only 30,000 donors have been registered (see, e.g., the Red Cross Website). In comparison, the National Marrow Donor Program (NMDP), a national registry of prospective bone marrow donors who have been genotyped for polymorphisms in certain loci of the Human Leukocyte Antigen (HLA) gene complex, in the year 2000, comprised 2.7 million fully characterized and 4.1 million known donors to supply matching bone marrow transplants for only ~2,400 transplantations per year. See, e.g., the National Marrow Donor Program Website Distribution of the precious few special units available in the program also leaves substantial room for improvement. At present, relying primarily on telephone contacts, only 1,000 special units are placed per year, while up to 2% of the approximately 4-5 million recipients of blood transfusions per year, that is 100,000 recipients, would benefit from improved availability.

In view of this situation, a method of providing a large and diverse inventory of fully typed blood units, and a method of instant and efficient distribution of units in response to requests posted to a central registry would be desirable in order to improve the public health and to minimize the cost accruing in the health care system in the form of unnecessarily prolonged hospital stays, adverse transfusion reactions (see Hillyer et al., Blood Banking and Transfusion Medicine; published by Churchill Livingston, Philadelphia Pa.) and other potential complications arising from allo-immunization.

However, absent substantial government or private funding for such an endeavor, a registry of "critical mass" must be created and operated in a commercially viable manner. The ARDP operation, representative of current practice, illustrates the difficulty: In order to identify a special donor, up to 1,000 donors may have been typed, and from a collection of 30,000 such special units, only 1,000 were placed. While special units fetch a higher price than do "vanilla" red blood cell products, the premium does not come close to covering the cost, in view of the substantial amount of excess typing required. Commercial viability, under these conditions, is doubtful.

SUMMARY

Described is the efficient organization and operation of a diverse registry of fully characterized blood units. Preferably, donors are characterized by DNA typing of the clinically most relevant genetic markers, including a set of mutations of Human Erythrocyte Antigens (HEA) including genetic variants of Rh, and additional antigens such as HLA and HPA. The registry, also referred to as a Transfusion Network, comprising certain application programs and databases preferably accessible via a web-browser interface, offers essentially instant access to linked inventories of typed units of donor blood ("actual" units) as well as access to genotyped donors who are available on-call ("callable" units), along with requisite information relating to donor status. Inventories of actual units or information relating to callable units can be held by subscribing member organizations, who also may participate in the operation and governance of the registry.

In a preferred embodiment, the registry network comprises an alliance of dominant regional and national donor centers (such as New York Blood Center and United Blood Services) which would set new standards in transfusion medicine. In another embodiment, regional donor centers and transfusion services are linked so as to create the critical mass of regional centers (both domestic and foreign) to decentralize the market by competing with the dominant national donor centers.

An "actively managed" registry—Existing registries such a the ARDP largely operate as passive repositories of donors encountered per chance during blood drives. Registries of bone marrow donors operated by the NMDP or comparable organizations around the world (REF), while in some cases actively funding bone marrow drives, operate in essentially the same manner of underwriting the large-scale typing of volunteer donors and collecting results. TO the extent that the population of donors and population of recipients are not balanced, this approach generally will be very inefficient from the point of view of maximizing the probability of a matching a recipient request.

To overcome this inefficiency, and to ensure commercial viability, a preferred strategy is described herein for constructing and maintaining a registry of genotyped donors which maximizes the number of units placed with the minimal number of candidate donors typed. To this end, relevant parameters relating to managing supply and forecasting demand are identified, and methods are described to optimize these parameters so as to maximize revenue and minimize total cost. The registry performs real-time analysis of supply and demand balance and directs its subscribing members to balance their respective donor typing operations.

A transfusion network, operated as an active registry, permits near-instant selection of prospective donors matching a given recipient by way of implementation on a global network such as the world wide web, thereby also facilitating the efficient distribution of units in inventory, further supported by transaction management including order placement and delivery. The registry will generate revenue from subscription as well as transaction fees, offering a set of products and services as described herein. Thus, a commercially viable registry, the first such in transfusion medicine, is disclosed, to improve clinical outcomes while enhancing economic efficiency.

In one embodiment, large-scale, rapid and cost-effective DNA typing, also herein referred as genotyping, of prospective donors is performed to permit instant matching of registered donors to recipients of known phenotype or genotype in a manner improving the clinical outcome of transfusion while improving economic efficiencies. To the extent that genotyped donors are retained, the cost of typing is minimized, as discussed herein.

The registry server preferably executes a "genetic crossmatching, gXM" algorithm to identify actual and callable donors within the registry. A gXM algorithm relating to a selection of the clinically most relevant human erythrocyte antigen (HEA) mutations is described in a co-pending application (see Provisional Application No. 60/621,196, entitled "A Method of Genetic Cross-Matching of Transfusion Recipients to Registered Donors," as well as applications to be filed claiming priority to it, all of which are incorporated by reference).

DETAILED DESCRIPTION

In order to maximize the economic efficiency of the transfusion registry, it will be preferable to adopt a strategy of minimizing the total number of donors typed for every recipient request fulfilled. The following exposition refers to a genotype to represent a combination of marker alleles, where, for each marker, the possible values of the allele are Normal (1), Homozygous (-1) or Heterozygous (0), and a specific genotype, representing a combination of alleles, thus has the form of a ternary string.

Estimating Demand: Requests for Special Units—In order to maintain a registry of candidate donors such that the maximal number of requests from prospective recipients for special units can in fact be matched while the number of excess donors typed is kept to a minimum, it will be critical to construct an estimate of anticipated demand.

Denote by:
$N^R$ the number of requests anticipated (or received);
$\lambda$ the probability of receiving ("logging") a request for a specific genotype;
$\mu$ the probability of matching a request (to a pre-determined level of resolution)

Available evidence indicates that the incidence of certain genotypes varies substantially between ethnic groups (see G. Hashmi et al., "A Flexible Array Format for Large-scale, Rapid Blood Group DNA Typing," Transfusion, in press). Therefore, the probability of a request for blood from a donor of specific genotype received from a random sample of a heterogeneous pan-ethnic population in fact represents a weighted average of probabilities, $\lambda_s$, for each of multiple constituent homogeneous subpopulations. The population-specific probabilities may be cast in the form:

$$\lambda_s \sim (N^{(Rs)}/N^{(R)}) f^{(s)} \Omega(r)$$

where $f^{(s)}$ represents the frequency of occurrence of a certain allele, the ratio $(N^{(Rs)}/N^{(R)})$ represents the relative proportion of individuals in subpopulation s within the pan-ethnic population at large, and $\Omega(r)$ represents a function of excess risk associated with a specific subpopulation (relative to the population at large). The function $\Omega(r)$, which may assume positive or negative values, reflects actuarial probabilities which in turn reflect genetic risk, e.g., the higher than average incidence of sickle cell anemia in African-Americans, or higher than average incidence of kidney disease in certain native American Indian tribes, requiring multiple transfusions, and environmental risk, e.g., the lower probability of, e.g., the Amish to suffer trauma in automobile accidents.

The probability, μ, of matching a specific request depends on the diversity of the registry and its linked inventories of actual and callable donors.

Managing Supply: Selection of Donors from Stratified Populations—In accordance with the preferred strategy of registry operation, the supply of registered donors will be adjusted to balance the anticipated demand.

Denote by:
N the number of new donors tested;
ε the fraction of special units encountered in a test population; $0 \leq \epsilon < 1$;
σ the fraction of special units sold.

The probability, σ, of selling any specific unit is determined, for given unit price, by the probability, μ, of matching a request for such a unit. Provided that an acceptable price for a unit is agreed upon, then:

$$\sigma = \mu$$

Preferably, the strategy for balancing the supply of registered donors will reflect the increased probability of finding an acceptable match for a prospective recipient of transfusion within a donor population of similar heritage. The similarity of genotype among individuals of similar heritage has been established for a variety of genetic markers such as those for certain inherited genetic disorders, including so-called Ashkenazi Jewish Diseases and Cystic Fibrosis (see, e.g., Jewish Virtual Library website), as well as for the highly variable human leukocyte gene complex which encodes for the human leukocyte antigens (HLA) determining the compatibility of recipients and donors of solid organs and bone marrow through the National Marrow Donor Program website. For blood group genotypes, but one example is provided by the high incidence in individuals of South Chinese heritage of the Miltenberger mutation within the MNS blood group (see M. Reid, "The Blood Group Antigen FactsBook" (2003)) which is largely absent in individuals of Caucasian heritage.

As with demand estimation, the probability of encountering a specific genotype in a pan-ethnic and hence genetically heterogeneous donor population will reflect the existence of constituent homogeneous subpopulations displaying varying values of that probability:

$$\epsilon = (N^{(1)}/N) f^{(1)} + (N^{(2)}/N) f^{(2)} + \ldots + (N^{(s)}/N) f^{(s)}$$

where, as before, $f^{(1)}, f^{(2)}, \ldots, f^{(s)}$ denote allele frequencies. To balance the supply of registered donors to anticipated demand, it will be desirable to select, for each subpopulation, s, shared among donor and recipient populations, the number of registered donors in accordance with the condition:

$$(N^{(s)}/N) = C(N^{(Rs)}/N^{(R)})\Omega(r)$$

The constant, C, captures factors such as the anticipated number of units required per recipient. This condition dictates that the registry, rather then genotyping all corners, would accept only a certain continent of donors from each subpopulation.

Factors determining Profitability—A key aspect of operating a transfusion registry network with an acceptable profit margin concerns the pricing for a test permitting the genotyping of a donor sample for a designated number of genetic markers, preferably by invoking elongation-mediated multiplexed analysis of polymorphisms ("eMAP"; as disclosed in U.S. application Ser. No. 10/271,602, incorporated by reference).

Denote by:
$N_k$ the number of new donors tested in year k, where $k=0, 1, 2, \ldots, n$;
$R_k$ the number of repeat donors (from year k-1) in year $k=1, 2, \ldots, n$;
ρ the fraction of repeat donors; generally $R_k < N_k$, and thus $\rho < 1$.
$\rho_s$ the fraction of repeat donors among special donors; $\rho_s < 1$.
ε the fraction of special units encountered in a test population; $0 \leq \epsilon < 1$;
c the cost of typing one sample;
σ the fraction of special units sold;
s the excess revenue (over the "vanilla" unit) of a special unit of product.

The cost of screening in year k is: $C_k = cN_k - g(R_k, R_{k-1} \ldots)$, that is, in any year but the first (k=0), the total cost of typing $N_k$ donor samples will be reduced by a certain portion reflecting the number of repeat donors from previous years. Various assumptions—manifesting themselves in specific forms of the function $g(R_k, R_{k-1}, \ldots)$—are possible. To the cost of typing must be added the cost of operating the registry—including transaction costs.

The revenue in year k reflects the sale of special units accumulated in inventory, that is: $S_k = h(N_k, N_{k-1}, \ldots)$. Various assumptions—manifesting themselves in specific forms of the function $h(N_k, N_{k-1}, \ldots)$—are possible.

The profit in year k is given by $P_k = S_k - C_k$. Break-even, $P_k = 0$, is attained at a certain k.

EXAMPLE 1

Single Repeat Donations

Assume that a certain constant total number of donors, say $N_0$, is screened every year, and that a (constant) fraction of donors repeat, but repeat only once, namely in the year following their initial donation. Then $R_k = \rho N_{k-1}$, and:

|  | Yr0 | Yr1 | Yr2 |
|---|---|---|---|
| New donors | $N_0$ | $N_1 = N_0 - R_1$ | $N_2 = N_0 - R_2$ |
| Repeat donors |  | $R_1 = \rho N_0$ | $R_2 = \rho N_1$ | where $R_2 = \rho N_1 = \rho(N_0 - R_1) = \rho N_0 - \rho^2 N_0$ and $N_2 = N_0 - \rho N_0 + \rho^2 N_0 = N_0(1 - \rho + \rho^2)$.

Generalizing, one finds the expression for $N_k$ to be $N_k = N_0(1 - \rho + \rho^2 - \rho^3 + \ldots)$; the alternating series reflects the fact that, as repeat donors stay away, a greater number of new donors must be screened in every even year. For n sufficiently large so that $\rho^{2n} \ll 1$, this expression turns out to be $N_k = N_0/(1+\rho)$, independent of n; for example, with $\rho = 1/2$, $\rho^{2n} = (1/2)^{2n} = 1/256$ for n=4.

Assume further that revenue in any given year reflects the sale of a certain fraction, σ, of the total units, $\epsilon N_0$, available that year, at an excess sales price, s, per sample, and that the population of repeat donors within the special population equals that within the general population. Then

| | Yr0 | Yr1 | Yr2 |
|---|---|---|---|
| | $S_0 = \sigma(\epsilon N_0)s$ | $S_1 = \sigma(\epsilon N_0)s$ | $S_2 = \sigma(\epsilon N_0)s$ |

Then $P_n = S_n - C_n = [\epsilon \sigma s - c/(1+\rho)] N_0$, independent of n. Under these assumptions, to attain break-even, $P_n = 0$, or $c/s = (1+\rho) \epsilon \sigma$, the cost per unit screened must not exceed a certain fraction of the excess revenue in each year.

For example, with reported numbers of $\Delta = 1/2$ (see Schreiber, G. B. et al., "Targeting Repeat Blood Donors Can Increase Supply," *Transfusion* 43: 591-97 (2003)), $=0.001$ (percentage of "rare" units in pan-ethnic population) and $\Phi = 1/5$, reflecting the placement of 1,000 "rare" units (from a stock of 30,000), with approximately 5,000 new rare units acquired per year (See, e.g., the National Marrow Donor Program Website), one obtains $c/s = 3/2*0.001*1/5 = 0.0003$. Since s will likely not exceed $1,000, the price per test will have to be negligibly small, not a scenario for a profitable large-scale screening operation. In fact, this is near the worst case scenario in which, along with the low abundance of special samples, and low percentage of placement, donors do not repeat ($\Delta = 0$).

It is anticipated that proper demand projection and inventory management, combined with providing instant access to such inventories by way of a transfusion registry network, as disclosed herein, will provide a basis to attain an operating regime of $\epsilon \to 0.1$ and $\rho \to 1$ so that, even with $\rho = 1/2$, $c/s = 3/2*0.1*1 = 0.15$.

EXAMPLE 2

Multiple Repeat Donations

In contrast to the previous Example 1, assume that of the total number of donors, say $N_0$, screened in the first year, a (constant) fraction of donors, once recruited, repeat every year. Given that each donor is genotyped only once, this will have a cumulative effect on cost reduction.

To illustrate the effect, assume first that the same fraction of general donors and special donors repeat, that is: $\rho = \rho_s$, and that this fraction is constant.

| | Yr0 | Yr1 | Yr2 |
|---|---|---|---|
| Cost | $C_0 = cN_0$ | $C_1 = c(N_0 - R_1)$ $= cN_0(1-\rho)$ | $C_1 = c(N_0 - R_2 - R_1)$ $= cN_0(1-\rho)^2$ |
| Revenue | $S_0 = \sigma(\epsilon N_0)s$ | $S_1 = \sigma(\epsilon N_0)s$ | $S_2 = \sigma(\epsilon N_0)s$ |

Then $P_n = S_n - C_n = [\epsilon \sigma s - c(1-\rho)^n] N_0$. The contrast to the model of Example 1 is dramatic: the requisite cost of typing required to attain the same revenue, decreases geometrically with n, the slope of the decrease being set by $\rho$. Break-even corresponds to $c/s = \epsilon \sigma/(1-\rho)^n$, and profit grows rapidly thereafter.

Figure 4:
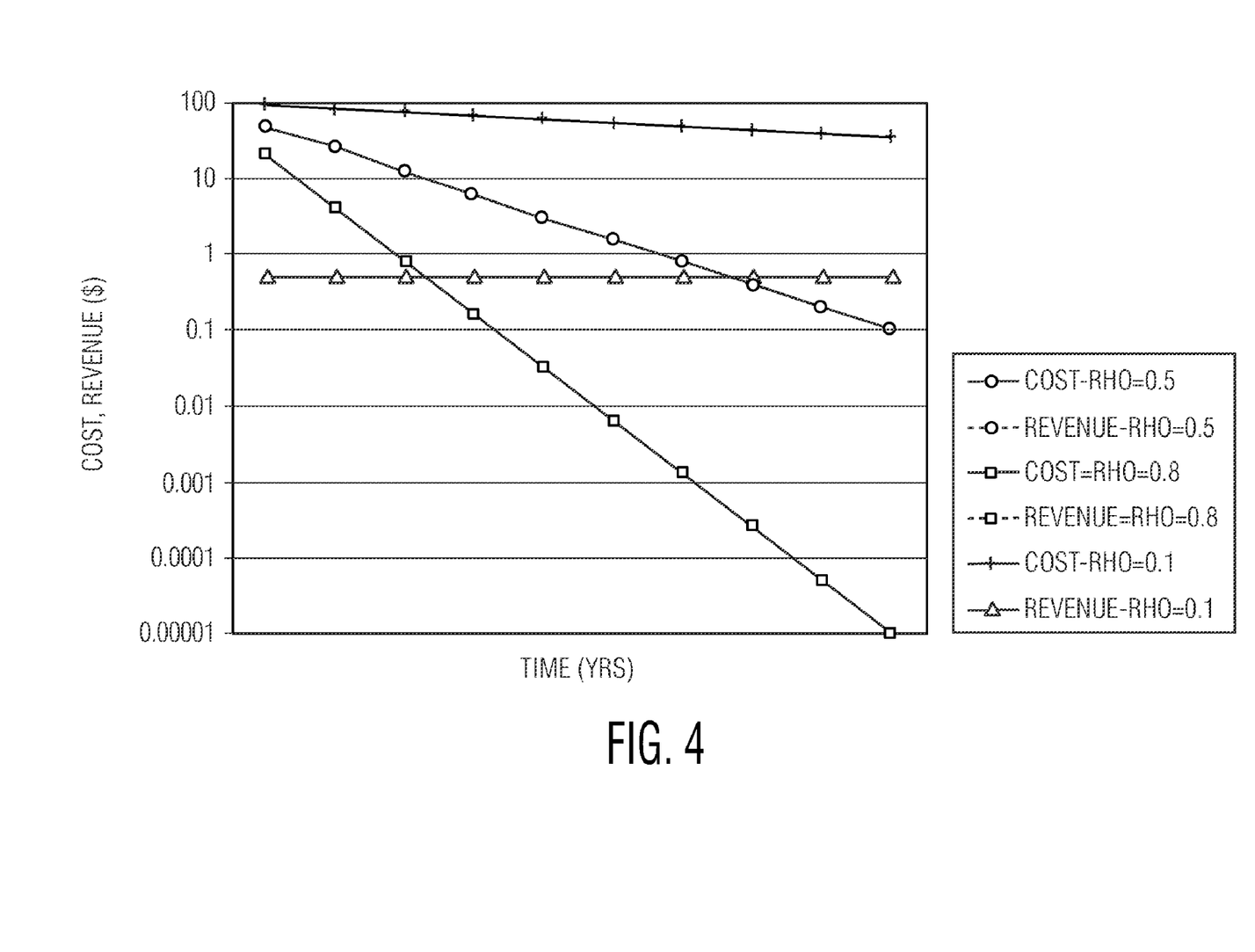
FIG. 4 is a graph showing the dependence of cost and revenue projections for a multiple donation scenario for various values of the repeat probability, RHO.

FIG. 4 illustrates the evolution of projected cost and excess revenue for different values of the repeat probability, $\rho$. Precedents for relatively high repeat probabilities exist, especially in donors who are aware of their special status. It will be desirable to provide incentives to such donors, as described below.

Figure 1:
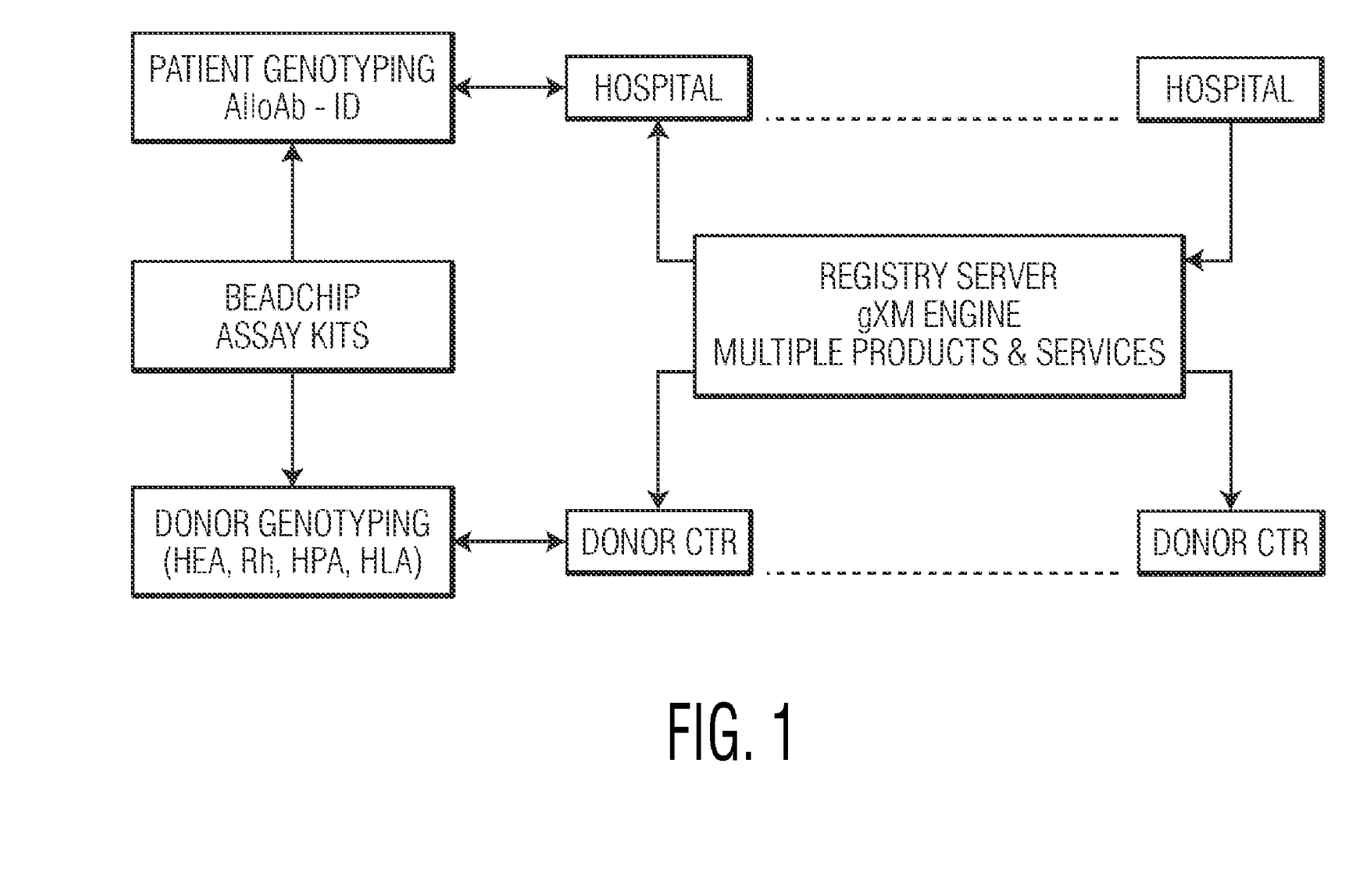
FIG. 1 is an illustration of a transfusion registry network linking multiple donor centers offering blood-derived products to multiple hospitals requesting blood-derived products for transfusion to patients. Participating parties can perform donor genotyping, patient genotyping and patient antibody screening (using, e.g., BeadChip™ assay kits). The registry performs genetic cross-matching and can offer a variety of additional products and services.
Figure 2A:
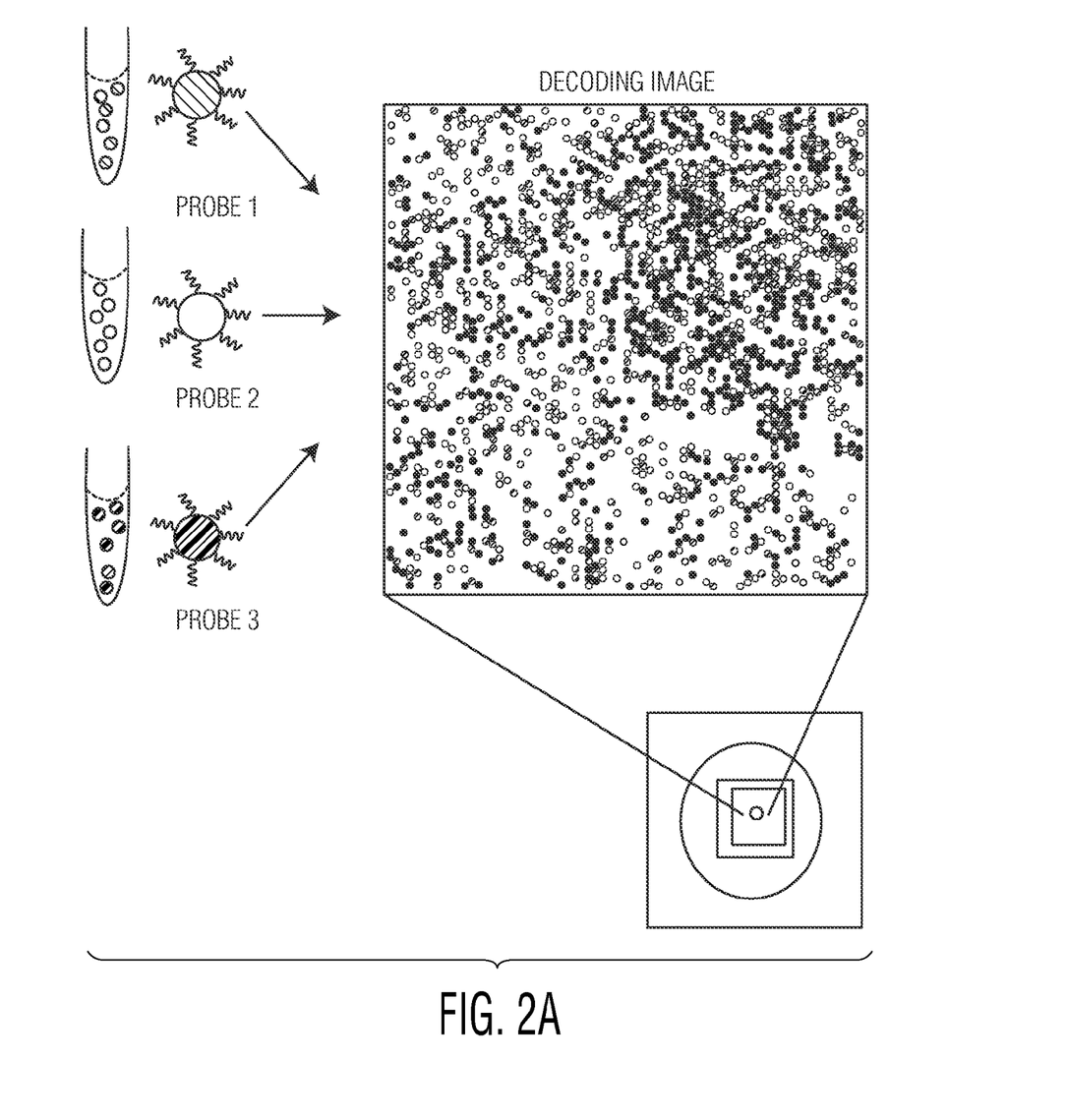
FIGS. 2A to 2D is a graphical depiction of the central components and subsystems of a BeadChip™ format for multiplexed analysis of polymorphisms and profiling of antibodies enabling the large-scale genotyping of donors and patients, as well as detection and identification of antibodies circulating in patient serum.
Figure 2B:
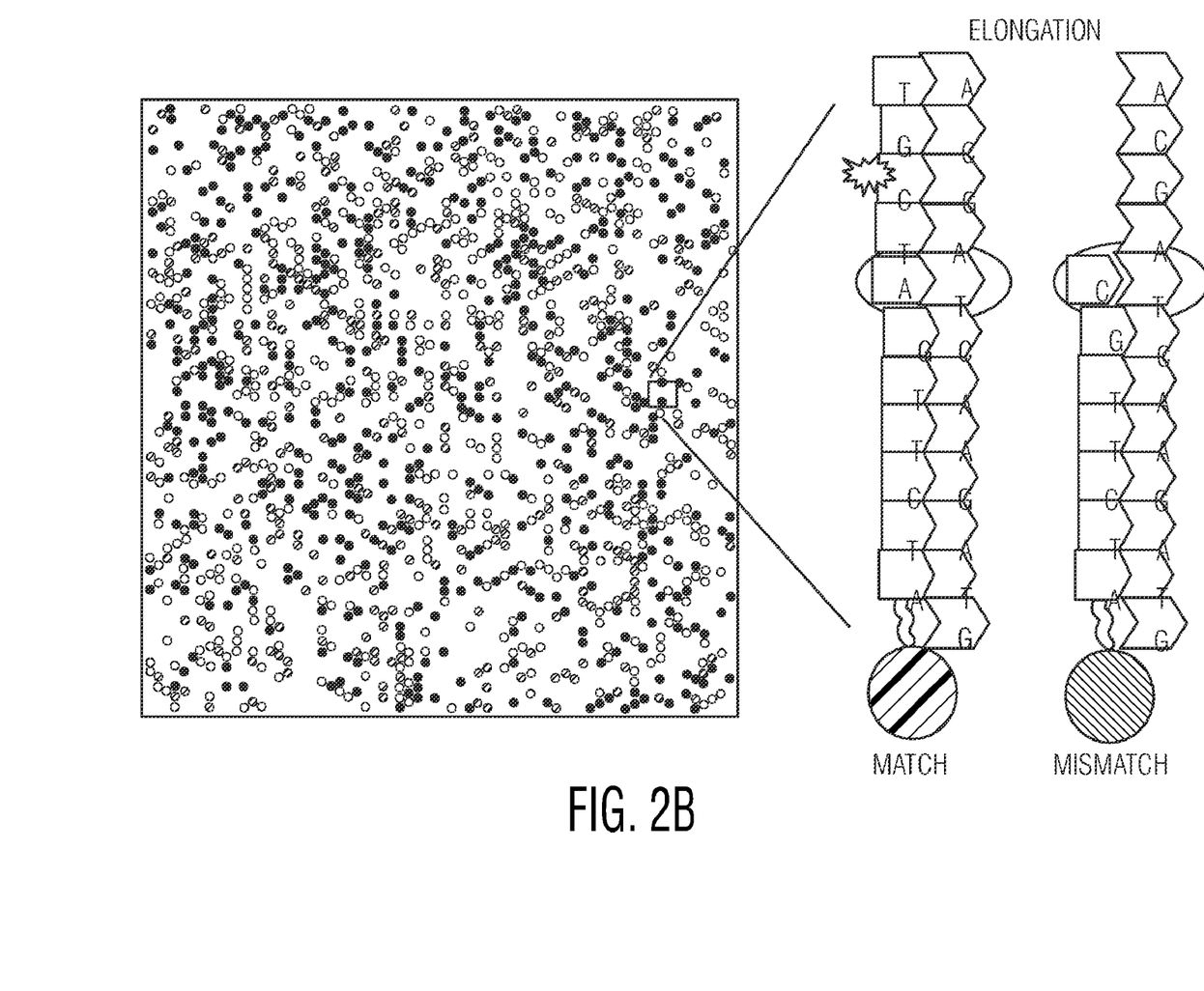
Figure 2C:
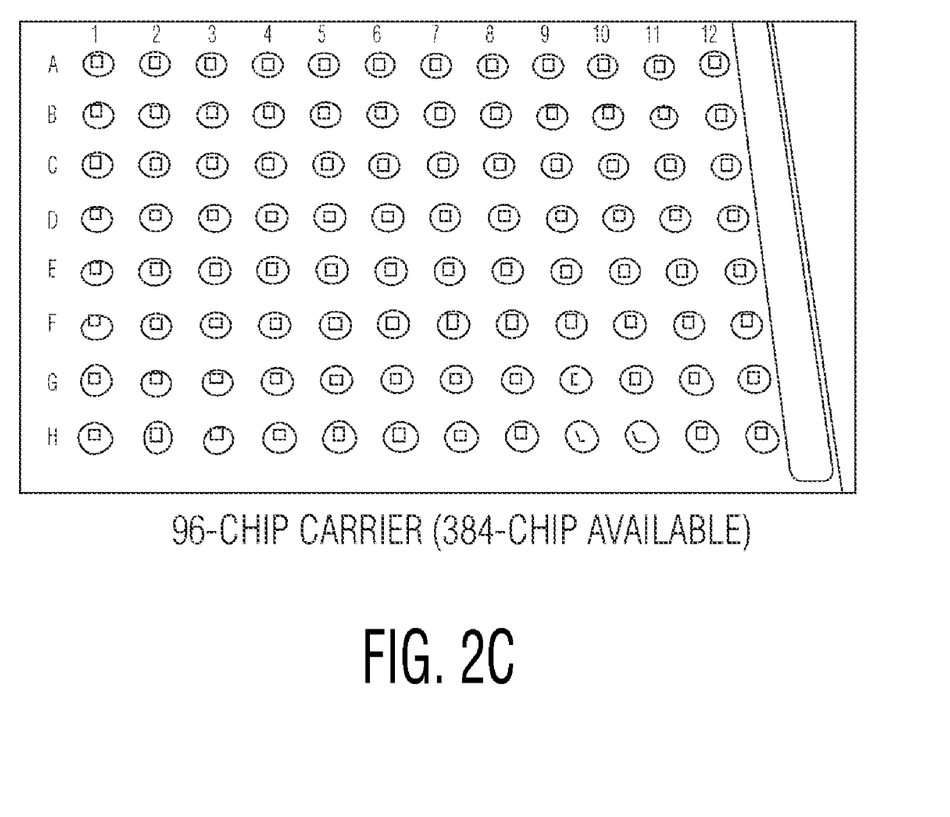
Figure 2D:
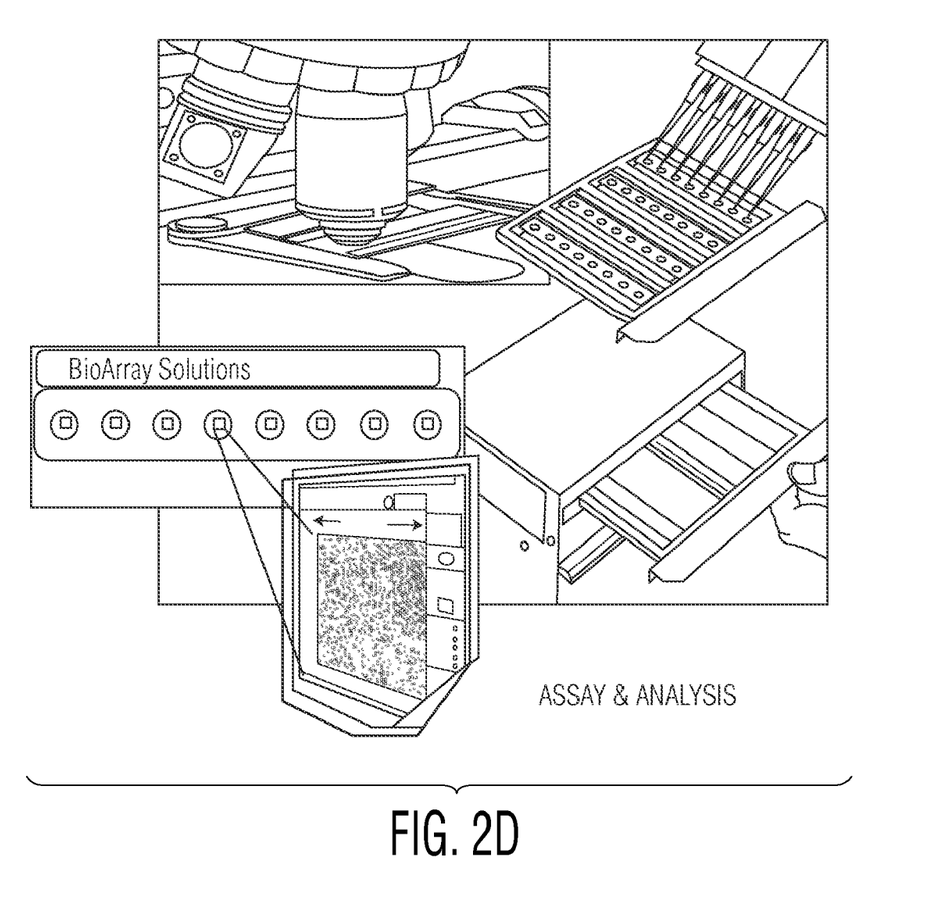
Figure 3:
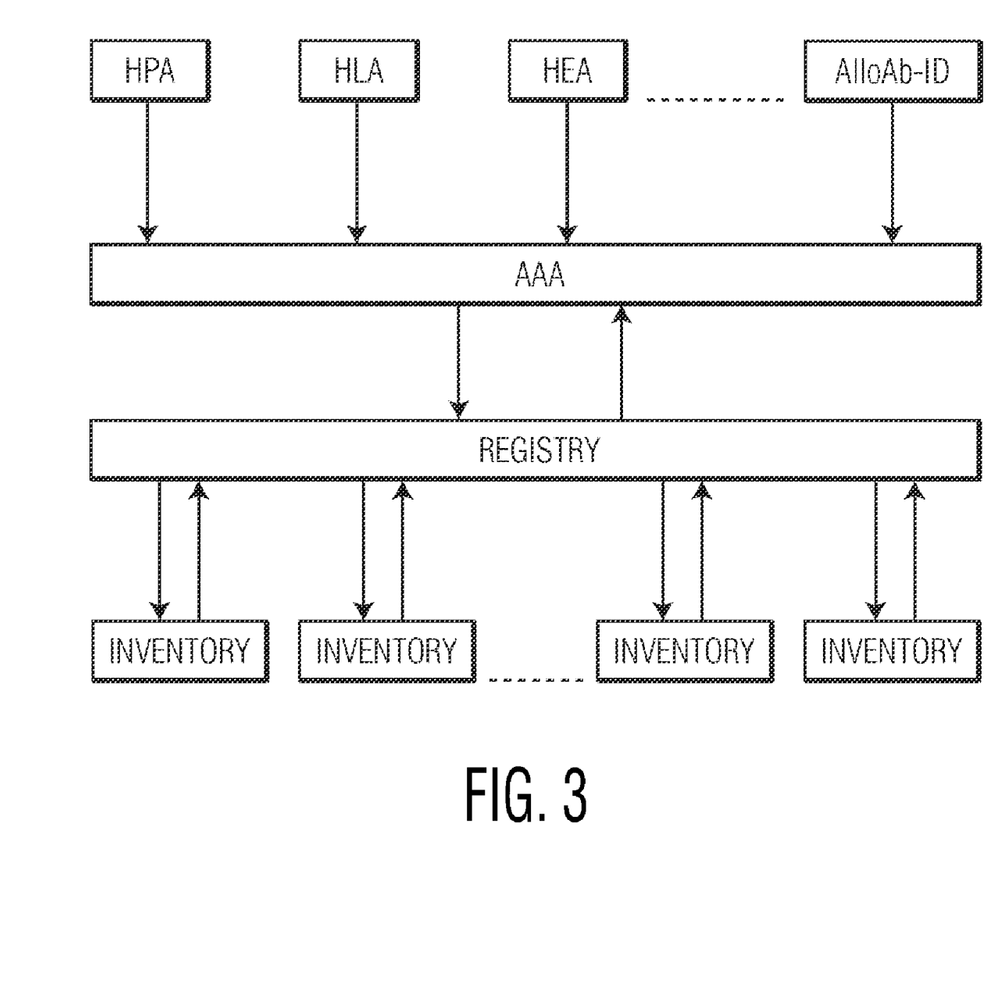
FIG. 3 is a graphical depiction of a uniform interface for presentation of data to the registry, preferably by way of a web-enabled Automated Allele Analysis (AAA) program (as disclosed in U.S. application Ser. No. 10/909,638, incorporated by reference), and the connection of the registry to linked inventories

Mutually Beneficial Interaction of Registry and Reagent Manufacturer—Provided that the large-scale genotyping of donors and patients is enabled by an efficient methodology, preferably invoking the eMAP-HEA design in conjunction with the BeadChip™ format (U.S. Provisional Application Ser. No. 60/586,931, entitled "Encoded Probe Pairs for Molecular Blood Group Antigen Molecular Typing and Identification of New Alleles" and applications claiming priority thereto (incorporated by reference); G. Hashmi et al., "A Flexible Array Format for Large-scale, Rapid Blood Group DNA Typing," Transfusion, in press; see also: FIG. 2), the cost of genotyping is reduced by the use of the multiplexed format of analysis and delivery of the assay in a parallel processing format, thereby permitting automation and uniform data management for a large menu of applications, including the typing of multiple antigen groups (FIG. 3).

In the initial stage, while building its initial donor reservoir, the registry, to the extent that it bears the cost of recruiting and genotyping donors, either directly, or indirectly, by way of subscribing member donor centers, will operate at a loss (FIG. 4). It will be beneficial for the registry to partner with a reagent manufacturer who would underwrite the operations in the initial stage, for example by providing kits at reduced or at no cost to the registry. To the extent that the registry is successful in retaining special donors, and hence reduces its cost of typing, the market opportunity for the reagent manufacturer declines. To compensate the reagent manufacturer, the registry could, for example, grant the manufacturer participation in a jointly controlled entity along with a profit sharing arrangement.

EXAMPLE 3

Expanding the Registry

The scenario of Example 2 offers several modes of operation. For example, the registry might operate in a "non-profit" regime by setting the ratio $c_n/s_n$ so as to ensure $P_n 0 = 0$. That is, the diagnostic reagent manufacturer, in return for obtaining a designated share of profits after break-even, can subsidize the initial ramp-up of the registry by accepting a lower price per test, corresponding to the condition $P_n(c_n/s_n) = 0$.

Alternatively, the registry, having attained breakeven, may decide to expand operations by expanding the number of donors screened per year, for example, such that the number of new donors is set by the available profit. This provides a mechanism to compensate the participating reagent manufacturer for the declining sales of tests arising from the successful retention of repeat donors.

Recruiting and Retaining Special Donors—The single repeat and multiple repeat scenarios indicate the critical role of the effect of the repeat probability on the profitability of the registry.

As with the recruitment of HLA donors for national registries, genotyping of blood group antigens will permit the identification of prospective future donors—that is, donors who do not have to donate blood until called upon. For example, analysis of DNA extracted from buccal swabs would enable "self-collection" in targeted communities such as churches and synagogues, and simple submission processes, e.g., by mail, to a designated member laboratory (not necessarily a donor center), for DNA analysis. This aspect not only allows the extension of the universe of known special donors, but also would be invaluable in registry management, in order to match the volume of donor typing to projected demand within individual subpopulations.

To refine this model toward a "best case" scenario, retention efforts would be directed to special donors, not the general donor population. The total number of special donors in each designated subpopulation would be matched to demand projections, as described above. Special donors would be given incentive to repeat by granting them, and donating family members, authorized direct emergency access to the registry.

Clinical Benefit vs. Cost of Genotyping: "Optimal" Panel Size—The clinical outcome of transfusion generally would improve with increasing resolution, that is, with the number of genetic markers included in the determination of patient and donor genotypes. The greatest benefit would derive from matching alleles encoding the clinically most significant blood group antigens (see M. Reid, "The Blood Group Antigen FactsBook" (2003)), and the incremental benefit of matching additional alleles would decrease. Ignoring cost, a reasonable criterion for the determining the optimal resolution would be to select this point of diminishing incremental benefit.

Figure 5:
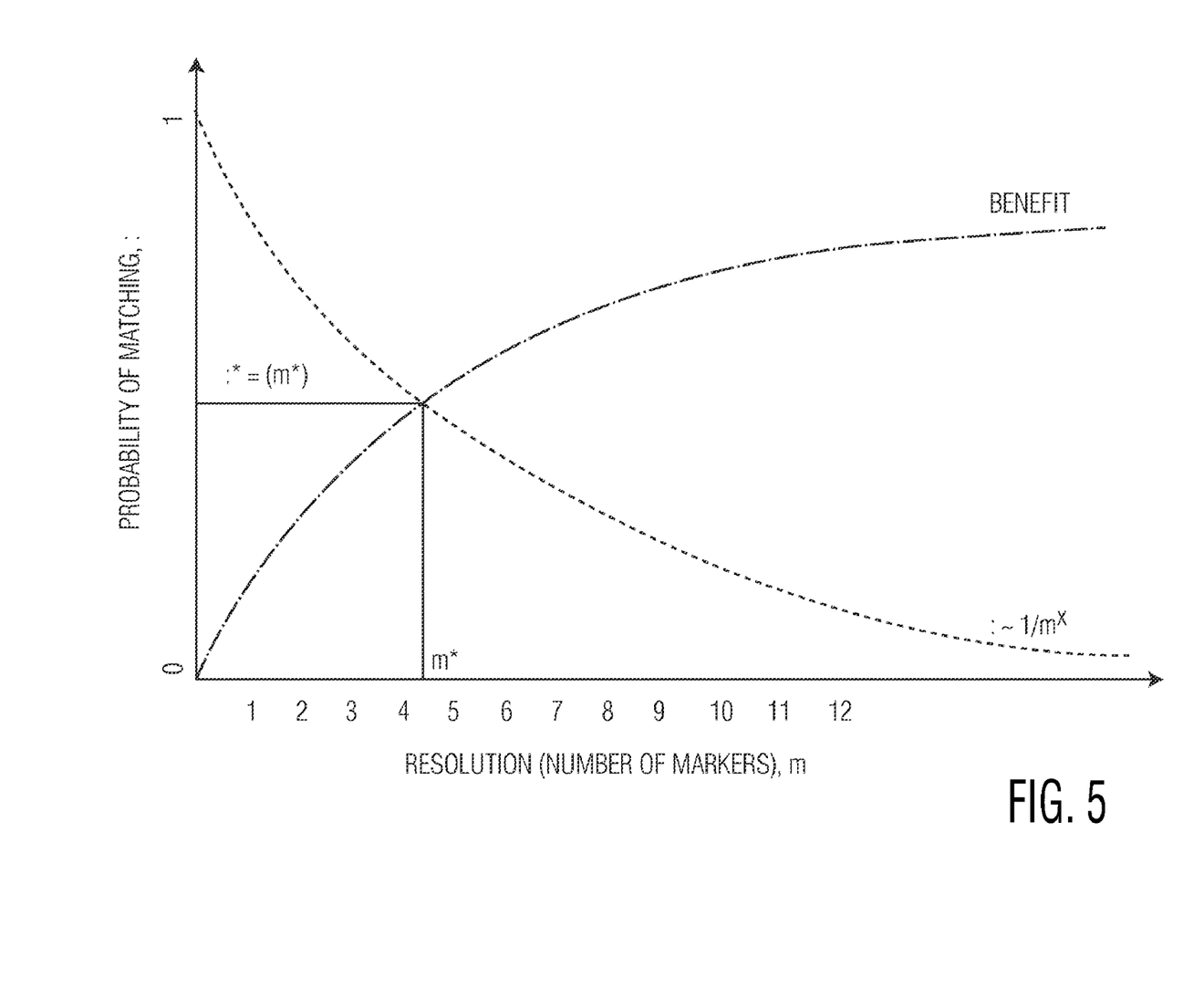
FIG. 5 is an illustration of the concept of optimal resolution (described in text).

However, significant economic considerations also apply. Thus, the higher the degree of resolution required for genetic cross-matching of a donor genotype to that of a patient, the higher the risk to the registry of not being able to place that unit, and the higher the cost of typing that unit. That is, c, the cost of genotyping, generally will increase with the number, m, of genetic markers included in the set, while the probability, $\mu$, of matching a request and selling a specific unit will decrease. For example, denoting by $f_{First}$, $f_{Second}$, $f_{Third}$, . . . $f_{Last}$ the relative allele frequencies of markers included in cross-matching, in the order of decreasing clinical significance, $\mu \sim f_{First}*f_{Second}*f_{Third}$, . . . $*f_{Last}$ thus $\mu \sim 1/m^x$, where x denotes an exponent, while $c \sim c_0 + a*m^y$, where $c_0$ denotes a constant, namely the initial cost of genotyping the first marker, a denotes a constant related to the marginal cost of genotyping additional markers, and y denotes an exponent reflecting the rate of increase in cost: for example, using a single-marker method of genotyping such as Restriction Fragment Length Polymorphism (RFLP) or Allele-specific PCR, one would anticipate cost to increase linearly, $y=1$, while using the preferred embodiment of elongation-mediated multiplexed analysis of polymorphisms (eMAP), one would anticipate cost to increase in a sublinear form, $y<1$. In either case, from the cost-benefit point of view, there exists an "optimal" resolution. Unless the market would compensate the registry for the higher cost of matching a donor unit to high resolution, in which case clinical benefit will set the optimal resolution, $m^*$, that value otherwise will be determined by the intersection of the two functions $\mu=\mu(m)$ and $c=c(m)$, as illustrated in FIG. 5.

Implementation of Registry—A co-pending application (U.S. application Ser. No. 10/909,638, incorporated by reference) discloses algorithms and implementations for automated allele analysis, and these methods are useful in connection with genetic cross-matching (gXM) generally, as disclosed in a further co-pending application (Provisional Application No. 60/621,196, noted above, incorporated by reference).

Using standard software engineering technologies such as MicroSoft.net ("dot-net"), these methods can be implemented in a manner permitting their use in an application-server modality using a standard web browser such as Microsoft Explorer™. Preferably, such an implementation, wAAA™, will invoke an SQL server and provide a uniform interface to Array Imaging Systems generating data for a variety of applications such as multiplex HEA, HLA and HPA analysis as well as patient and donor antibody identification. As disclosed in a co-pending application (Ser. No. 10/714,203), data records will be uploaded—preferably using transaction protocols preserving donor and patient anonymity—to the wAAA application on a central server permitting review and redaction by, and delivery to authorized users.

Establishing an Efficient Market: Management of Real-time Transactions—Disclosed is a mode of operating a commercially viable registry in the form a real-time transaction network offering instant access to a diverse collection of characterized donors, that is, both actual donor-derived blood products in linked inventories, and callable candidate donors of desirable genotype. Such a registry will increase demand by extending its reach to a global base of potential customers by providing access to its products and services by way of a standard web browser and permitting applications, notably automated allele analysis, gXM and selection of candidate donors to be performed automatically, in real time. By offering instant transactions, under a variety of pricing arrangements including contracts, notably futures contracts, as well as real-time pricing, for example by way of bid-ask matching (currently available in the context of web-auctions as well as Electronic Communications Networks (ECNs), the registry will create an efficient market.

Collection of Samples, Assay Performance, Analysis of Assay Results, Patient Counseling and Reporting Results to Patients—Also disclosed herein is a model of implementing molecular diagnostics in a mode of "virtual centralization" which permits the the steps of actually performing assays, preferably in a standard and universal format such as the Random Encoded Array Detection (READ™) format, and the steps of analyzing, interpreting and reporting assay results including communicating outcomes to the patient or referring physician, to be performed in different locations, such that experts or groups of experts have access, by way of a standard web browser to the wAAA environment to review data generated in a location different from their own physical location.

Virtual centralization of the data is accomplished by uploading of data relating to assay results, and interpretation/analysis thereof, to a server or other accessible database. It can then be accessed by or securely transmitted to authorized parties to perform additional interpretation or analysis, or to view or report the results. User identification can be secured at all stages of the process so as to preserve confidentiality, such that, for example, only the patient and perhaps his physician will be aware of the patient identity associated with particular results.

This model is particularly well-suited to the analysis and interpretation of results produced by genetic tests, including, results which can be processed for initial analysis by the web-based AAA program (discussed above) or where these results are in the form of images for which standard formats of network transmission now exist. Assay formats producing suitable images invoke, for example, spatially encoded "dot blot" or "reverse dot blot" formats, including "spotted" probe or protein arrays; arrays of oligonucleotide probes synthesized in-situ on a substrate; or probes (or proteins) associated with encoded beads; see U.S. Pat. No. 6,797,524; U.S. application Ser. No. 10/204,799, filed on Aug. 23, 2002 "Multianalyte Molecular Analysis Using Application-Specific Random Particle Arrays," (incorporated by reference).

Networking allows the different parties involved in different steps of the process to perform their respective functions such as collecting samples, performing the assay, or analyzing the results, at the same location, or at different locations. Performing separate functions by different parties at different locations can provide a significant advantage in terms of cost and speed of analysis, as parties do not need to travel to a location to carry out their function. It also allows better control over the confidentiality of the results, as results do not need to be physically transported, by non-secure means, to different locations.

After sample collection, or self-collection by the patient (e.g., by using a buccal swab), an assay on a patient sample can be performed at a first location. The initial assay results, which may be encoded (see U.S. Pat. No. 6,797,524; U.S. application Ser. No. 10/204,799, filed on Aug. 23, 2002 "Multianalyte Molecular Analysis Using Application-Specific Random Particle Arrays," both being incorporated herein by reference) or in the form of an assay image (see "Analysis, Secure Access to and Transmission of Array Images," Ser. No. 10/714,203, filed Nov. 14, 2003, incorporated herein by reference), can be uploaded to a server or transmitted to an analysis site (which may be the site which sold the assay kit to the remote location). The identity of the patient can be associated with the sample, using, e.g., methods set forth in the co-pending application "Genetic Analysis and Authentication," Ser. No. 10/238,439 (incorporated herein by reference). The analysis site decodes or interprets or performs a preliminary analysis of the results (and/or the assay image), and may also obtain assistance in interpretation from experts or consultants, who may either be on-site or may transmit an image from the assay, or who have access to the server with such images or results. The analyzed results can then be accessed by, or transmitted to, the patient's physician, or the patient, or the laboratory where the assay was conducted, which in turn provides them to the patient's physician and/or the patient. It is possible to keep the patient identity separated from the results at all stages, so that only the physician and the patient, or even only the patient, can correlate results with a particular patient. This secures the confidentiality of assay information, as is desirable in the case of genetic information, given the growing concern over maintaining confidentiality of individual's genetic data.

In this manner, the "front-end" of laboratory practice is standardized, preferably by adoption of a BeadChip™ format of performing multiplexed nucleic acid and protein analysis while the "back end", generally requiring specialized expertise, is moved to a network, preferably by implementation of an application service which provides network protocols to transmit assay results, perform analysis, authorize access to databases for review and result certification, and manage communication between multiple participants in the process.

It should be understood that the terms and expressions herein are exemplary only, and not limiting, and that the invention is defined only in the claims which follow, and includes all equivalents of the claimed subject matter.

What is claimed is:

1. A method for reducing the incidence of allo-immunization in recipients transfused by samples obtained from member institutions below that otherwise experienced, where member institutions form a registry which retains a database of genotyped donors, and where certain member institutions perform transfusions to recipients, comprising:
    requiring that certain member institutions genotype donors for certain molecular markers associated with clinically significant events;
    maintaining the genetic marker information associated with the genotyped donors and the samples which they donate;
    requiring that certain member institutions genotype or phenotype recipients for said markers; and
    transfusing blood, serum or tissues to recipients only if the donor genotype precludes the expression of said molecular markers by said donors.

2. The nethod of claim 1 wherein the molecular markers relate to blood group antigen groups including RhCE, Kidd, Kell, Duffy, Dombrock, MNS, and combinations of markers from RhCE, Kidd, Kell, Duffy, Dombrock and MNS.

* * * * *

UNITED STATES PATENT AND TRADEMARK OFFICE
CERTIFICATE OF CORRECTION

PATENT NO.        : 7,363,170 B2                                            Page 1 of 1
APPLICATION NO.   : 11/092420
DATED             : April 22, 2008
INVENTOR(S)       : Michael Seul and Robert James Danegy It is certified that error appears in the above-identified patent and that said Letters Patent is hereby corrected as shown below:

Claim 1, column 12, line 33, after the word "recipients" and before "if", delete "only"

Signed and Sealed this

Second Day of September, 2008

JON W. DUDAS
*Director of the United States Patent and Trademark Office*